(12) United States Patent
Tolles

(10) Patent No.: US 6,623,341 B2
(45) Date of Patent: Sep. 23, 2003

(54) SUBSTRATE POLISHING APPARATUS

(75) Inventor: Robert D. Tolles, Santa Clara, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 10/087,502

(22) Filed: Feb. 28, 2002

(65) Prior Publication Data

US 2002/0132569 A1 Sep. 19, 2002

Related U.S. Application Data

(62) Division of application No. 09/484,867, filed on Jan. 18, 2000, now Pat. No. 6,533,645.

(51) Int. Cl.$^7$ ............................................... B24B 29/00
(52) U.S. Cl. ...................... 451/288; 451/532; 451/443
(58) Field of Search ................... 451/285, 286, 451/287, 288, 56, 60, 527, 532, 538; 51/296, 298, 307

(56) References Cited

U.S. PATENT DOCUMENTS

| | | |
|---|---|---|
| 4,728,552 A | 3/1988 | Jensen, Jr. |
| 4,841,680 A | 6/1989 | Hoffstein et al. |
| 4,927,432 A | 5/1990 | Budinger et al. |
| 5,152,809 A | 10/1992 | Mattesky |
| 5,152,917 A | 10/1992 | Pieper et al. |
| 5,197,999 A | 3/1993 | Thomas |
| 5,257,478 A | 11/1993 | Hyde et al. |
| 5,342,419 A | 8/1994 | Hibbard |
| 5,348,615 A | 9/1994 | Gupta |
| 5,378,251 A | 1/1995 | Culler et al. |
| 5,489,233 A | 2/1996 | Cook et al. |
| 5,578,362 A | 11/1996 | Reinhardt et al. |
| 5,605,760 A | 2/1997 | Roberts |
| 5,900,164 A | 5/1999 | Budinger et al. |
| 5,916,010 A | 6/1999 | Varian et al. |
| 6,022,264 A | 2/2000 | Cook et al. |
| 6,022,265 A | 2/2000 | Drill et al. |
| 6,022,268 A | 2/2000 | Roberts et al. |
| 6,069,080 A | 5/2000 | James et al. |
| 6,099,387 A | 8/2000 | Gilmer et al. |
| 6,099,394 A | 8/2000 | James et al. |
| 6,106,754 A | 8/2000 | Cook et al. |
| 6,120,353 A | 9/2000 | Suzuki et al. |
| 6,139,406 A | 10/2000 | Kennedy et al. |
| 6,217,434 B1 | 4/2001 | Roberts et al. |
| 6,227,947 B1 * | 5/2001 | Hu et al. ........................ 451/56 |
| 6,227,948 B1 * | 5/2001 | Khoury et al. ................. 451/56 |
| 6,231,434 B1 | 5/2001 | Cook et al. |
| 6,287,185 B1 | 9/2001 | Roberts et al. |
| 6,293,852 B1 | 9/2001 | Roberts et al. |

FOREIGN PATENT DOCUMENTS

EP        1 113 099 A2        7/2001

* cited by examiner

Primary Examiner—Dung Van Nguyen
(74) Attorney, Agent, or Firm—Fish & Richardson (57) ABSTRACT

A polishing material for chemical mechanical polishing has a mesh of fibers and a binder material holding the fibers in the mesh. The binder material coalesced among the fibers to leave pores in the interstices between the fibers of the mesh. The fibers and binder material provide the polishing material with a brittle texture. The fibers can be cellulose, and the binder material can be a phenolic resin.

26 Claims, 5 Drawing Sheets

PHENOLIC PAPER LAMINATE

MAG = 60.0X

FIG._8A

PHENOLIC PAPER LAMINATE

MAG = 200.0X

FIG._8B

SUBSTRATE POLISHING APPARATUS

CROSS-REFERENCE TO RELATED APPLICATIONS

This application is a division of U.S. patent application Ser. No. 09/484,867, filed on Jan. 18, 2000, now U.S. Pat. No. 6,533,645, the entire disclosure of which is incorporated herein by reference.

BACKGROUND

The invention relates to chemical mechanical polishing of substrates, and more particularly to an article and method for polishing a substrate.

Integrated circuits are typically formed on substrates, particularly silicon wafers, by the sequential deposition of conductive, semiconductive or insulative layers. After each layer is deposited, it is etched to create circuitry features. As a series of layers are sequentially deposited and etched, the outer or uppermost surface of the substrate, i.e., the exposed surface of the substrate, becomes increasingly nonplanar. This nonplanar surface presents problems in the photolithographic steps of the integrated circuit fabrication process. Therefore, there is a need to periodically planarize the substrate surface to provide a planar surface. Planarization, in effect, polishes away a non-planar, outer surface, whether a conductive, semiconductive, or insulative layer, to form a relatively flat, smooth surface.

Chemical mechanical polishing is one accepted method of planarization. This planarization method typically requires that the substrate be mounted on a carrier or polishing head with the exposed surface of the substrate placed against a rotating polishing pad or moving polishing belt (both of which will be referred to herein as polishing pads). The polishing pad may be either a "standard" pad or a fixed-abrasive pad. A conventional standard pad is formed of a durable material, whereas a fixed-abrasive pad has abrasive particles held in a containment media. The carrier head provides a controllable load, i.e., pressure, on the substrate to push it against the polishing pad.

A polishing slurry, including at least one chemically-reactive agent (e.g., deionized water for oxide polishing), and abrasive particles (e.g., silicon dioxide for oxide polishing) if a standard pad is used, is supplied to the surface of the polishing pad. The slurry can also contain a chemically reactive catalyzer (e.g., potassium hydroxide for oxide polishing).

One conventional polishing pad, described in U.S. Pat. Nos. 5,578,362 and 5,900,164, is a hard composite material with a roughened polishing surface. This polishing pad is composed of solid cast block of durable urethane mixed with fillers, such as hollow microcapsules, which provide the polishing pad with a microporous texture. The polishing pad has a low compressibility, is plastically deformable, and has a relatively low tensile modulus. This polishing pad is available from Rodel, Inc., located in Newark, Del., under the trade name IC-1000.

Another conventional polishing pad, described in U.S. Pat. Nos. 4,728,552 and 4,927,432 is a soft composite material with a compliant polishing surface. This polishing pad is composed of a dense net or mesh of polyester fibers, such as Dacron™, oriented substantially perpendicular to the polishing surface of the pad and leached or impregnated with urethane. The urethane fills a significant fraction of the void space between the fibers. The resulting pad is relatively compressible, is plastically and elastically deformable, and has a relatively low tensile modulus. This polishing pad is available from Rodel, Inc., under the trade name Suba-IV A two-layer polishing pad, described in U.S. Pat. No. 5,257,478, has an upper layer composed of IC-1000 and a lower layer composed of SUBA-IV. The polishing pad may be attached to a rotatable platen by a pressure-sensitive adhesive layer.

Yet another conventional polishing pad, described in U.S. Pat. No. 4,841,680, is soft poromeric material with a compliant polishing surface. This polishing pad is composed of a urethane with tubular void structures oriented perpendicularly to the polishing surface to provide the polishing pad with a spongelike texture. The resulting pad is relatively soft, and has a relatively low elastic modulus. This type of polishing pad is available from Rodel, Inc., under the trade name Polytex.

A conventional fixed abrasive polishing pad includes discrete islands or blocks of polishing material formed on a multilayer sheet. The islands of polishing material are composed solid blocks of resin in which abrasive particles, such as silicon, aluminum or cerium particles, are dispersed. The resulting pad, although flexible, is relatively non-compressible and inelastic. As a substrate is polished, the resin is worn away to continuously expose additional abrasive particles. Fixed abrasive polishing pads are available from 3M, Inc., located in Minneapolis, Minn.

The effectiveness of a CMP process may be measured by its polishing rate and by the resulting finish (roughness) and flatness (lack of large-scale topography) of the substrate surface. Inadequate flatness and finish can produce device defects. The polishing rate sets the time needed to polish a layer and the maximum throughput of the polishing apparatus.

One limitation on polishing throughput, particularly when IC-1000 is used as the polishing material, is "glazing" of the polishing pad surface. Glazing occurs when the polishing pad is frictionally heated, shear stressed, and compressed in regions where the substrate is pressed against it. The peaks of the polishing pad are pressed down and the pits of the polishing pad are filled up, so the surface of the polishing pad becomes smoother and less able to transport slurry. As a result, the polishing time required to polish a substrate increases. Therefore, the polishing pad surface must be periodically returned to an abrasive condition, or "conditioned", to maintain a high throughput. The conditioning process is destructive and reduces the lifetime of the polishing pad.

Another limitation on throughput is the lifetime of the polishing pad. If a polishing pad wears out, it needs to be replaced. This requires that the polishing machine be shut down temporarily while a new polishing pad is affixed to the platen. The typical lifetime of an IC-1000 polishing pad is about 400–800 wafers.

An additional consideration in the production of integrated circuits is process and product stability. To achieve a low defect rate, each substrate should be polished under similar conditions. However, the mechanical properties of a set of polishing pads can vary from pad to pad. In addition, changes in the process environment during polishing, such as temperature, pH, and the like, can alter or degrade the polishing pad, thereby leading to variations in the mechanical properties of the pad from substrate to substrate. This variability may lead to substrate surface variability.

Another consideration about conventional polishing pads is effective slurry transport. Some polishing pads, particularly pads with a solid non-porous polishing surface, such as the IC-1000, do not effectively or uniformly transport slurry. A result of ineffective slurry transport is non-uniform polishing. Grooves or perforations may be formed in a polishing pad to improve slurry transport.

SUMMARY

In general, in one aspect, the invention is directed to a method of chemical mechanical polishing. In the method, a substrate is brought into contact with a material that includes a mesh of fibers and a binder holding the fibers in the mesh, an abrasive slurry to the interface between the substrate and the material, and relative motion is created between the substrate and the material. The binder is coalesced among the fibers to leave pores in the interstices between the fibers of the mesh. The fibers and binder provide the material with a brittle structure.

Implementations of the invention may include one or more of the following features. The material formed by the fibers and binder may have a tensile modulus greater than about $10^5$ psi, e.g., greater than about $3 \times 10^5$ psi. The material formed by the fibers and binder may elongate less than about 5%, such as less than 2%, e.g., less than about 1% before breaking. The material may undergo elastic deformation during compression. The fibers may include cellulose, e.g., linen, cotton or wood, or a polyamide, e.g., Aramid. The binder may include a resin, e.g., a phenolic resin. The ratio of fibers to binder in the material may be about 1:1 to 2:1 by weight. The pores may occupy about half of the volume of the material. The fibers may be oriented substantially randomly throughout the material. The material includes one or more of the following: graphite, calcium celite, and an elastomer.

In another aspect, the invention is directed to a method of chemical mechanical polishing in which a semiconductor wafer is brought into contact with an automotive brake or clutch pad. An abrasive slurry is supplied to the interface between the wafer and the pad, an relative motion is created between the wafer and the pad.

In another aspect, the invention is directed to an article for chemical mechanical polishing of a substrate. The article has a layer of polishing material with a mesh of fibers and a binder material holding the fibers in the mesh, and a polishing surface to contact and polish a substrate. The binder material is coalesced among the fibers to leave pores in the interstices between the fibers of the mesh. The fibers and binder material provide the polishing material with a brittle structure.

In another aspect, the invention is directed to an article for polishing of a substrate. The article has a layer of polishing material having a mesh of fibers and a binder material holding the fibers in the mesh, and a polishing surface to contact and polish a substrate. The binder material is coalesced around the fibers to leave pores in the interstices in the fiber mesh. At least the binder material is sufficiently brittle that a lateral force created by relative motion between a substrate and the polishing surface tends to cause fragments of the fibers and the binder material at the surface to break away from the layer of polishing material.

In another aspect, the invention is directed to an article for polishing of a substrate. The article has a layer of polishing material with a mesh of cellulose fibers and a phenolic resin binding the fibers in the mesh, and a polishing surface to contact and polish a substrate. The resin is coalesced around the fibers to leave pores in the interstices in the fiber mesh.

In another aspect, the invention is directed to a chemical mechanical polishing apparatus. The apparatus has a carrier head to hold a substrate, a polishing pad, and a slurry supply port to dispense a polishing slurry to the polishing pad. The polishing pad includes a mesh of fibers and a binder material holding the fibers in the mesh. The binder material coalesced among the fibers to leave pores in the interstices between the fibers of the mesh, and the fibers and binder material provide the polishing pad with a brittle structure.

Implementations of the invention may include one or more of the following features. The polishing pad may be secured to a surface of a rotatable platen. The apparatus may have a plurality of nozzles to spray a cleaning solution onto the polishing pad and remove slurry from the polishing pad. The apparatus may also have a plurality of nozzles to direct jets of air onto the polishing pad and remove the cleaning solution from the polishing pad.

In another aspect, the invention is directed to a method of forming a polishing material. In the method, a liquid binder material is mixed with fibers to form a pulp. The pulp is dried to cure the binder material and create a composite material including a fiber mesh held by the binder material, with the binder material coalesced among the fibers to create a leave pores in the interstices between the fibers of the mesh and the composite material being relatively brittle.

Implementations of the invention may include one or more of the following features. The pulp may be compressed to remove liquid from the polishing material. The pulp may be deposited onto a moving screen.

In another aspect, the invention is directed to a chemical mechanical polishing apparatus that has a first piece of a polishing material, a carrier to hold a substrate in contact with a surface of the first piece of the polishing material, and a conditioner apparatus. The conditioner apparatus has a second piece of the polishing material movable into contact with the surface of the first piece of polishing material.

Implementations of the invention may include one or more of the following features. The apparatus may include a slurry dispensing port to provide an abrasive slurry to the surface of the first piece of polishing material, and means for causing relative motion between the first piece of polishing material and the substrate. The conditioner apparatus may include a rotatable conditioner head to which the second piece of polishing period is attached. The conditioner apparatus may include an arm to move the conditioner head laterally across the first piece of polishing material.

In another aspect, the invention is directed to a method of chemical mechanical polishing in which a substrate is brought into contact with a first polishing surface that includes a polishing material, relative motion is caused between the substrate and the polishing surface, and the polishing surface is conditioned with the same material as the polishing surface.

In another aspect, the invention is directed to a method of chemical mechanical polishing. In the method, a slurry is supplied to a polishing pad that has a plurality of pores therein. A substrate is brought into contact with a polishing surface of the polishing pad, and relative motion is caused between the substrate and the polishing surface. A spray of a cleaning liquid is directed onto the pad to remove slurry from the pores, and a jet of gas is directed onto the polishing pad to remove the cleaning liquid from the pad.

Advantages of the invention may include one or more of the following. The polishing pad can be fabricated using techniques that are conventional in the automobile clutch and brake pad industry, and can have a low manufacturing cost. The polishing pad can have an intrinsically long lifetime, and may not need conditioning. This also permits the polishing apparatus to be constructed without a conditioner apparatus, thereby reducing the cost and complexity of the polishing apparatus. If the polishing pad is conditioned, it can be conditioned with another piece of polishing pad rather than a diamond-coated disk, thus reducing the cost of the conditioning device. The polishing pad can provide uniform material properties as it is worn away, thus providing a uniform polishing rate throughout the lifetime of the pad. The polishing pad is unlikely to cause scratching of the substrate. The polishing pad can be wetable and can effectively transport slurry without grooves or perforations. The polishing pad can be mounted to a platen without a subpad. The polishing pad can be thermally stable over a wider range of temperatures than conventional pads, thereby improving polishing uniformity. The polishing pad can be formed with a roughness or surface friction sufficient to provide a satisfactory polishing rate.

Additional features and advantages of the invention will become apparent from the following description including the drawings and the claims.

DETAILED DESCRIPTION

Figure 1:
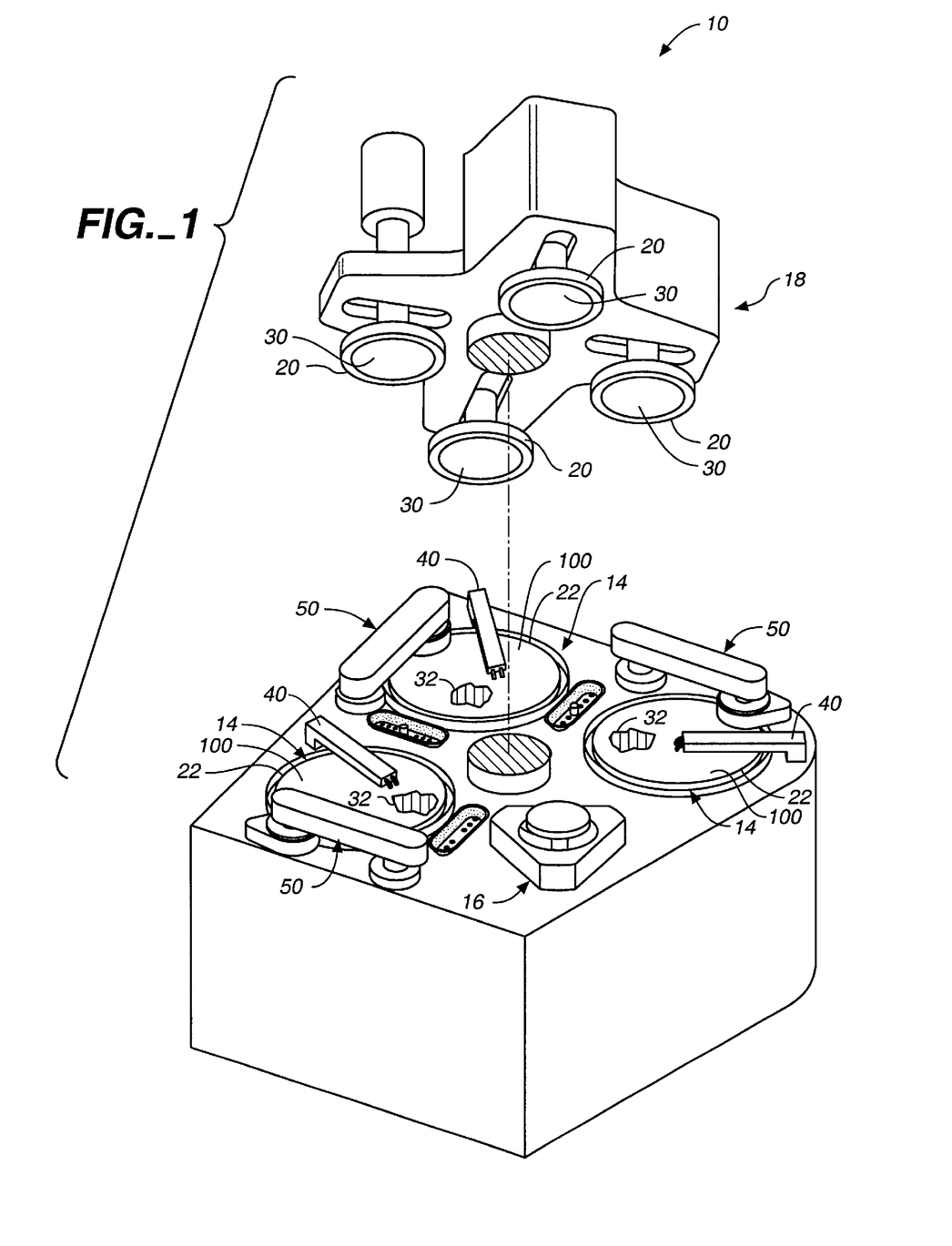
FIG. 1 is a schematic perspective view, partially exploded, of a chemical mechanical polishing apparatus.

Referring to FIG. 1, a polishing apparatus 10 includes three independently-operated polishing stations 14, a substrate transfer station 16, and a rotatable carousel 18 which choreographs the operation of four independently rotatable carrier heads 20. A description of a similar polishing apparatus may be found in U.S. Pat. No. 5,738,574, the entire disclosure of which is incorporated herein by reference.

Each polishing station 14 includes a rotatable platen 22 that supports a polishing pad 100. As will be explained in detail below, the polishing pad 100 is formed of a fiber matrix held with a resin binder.

In operation, a substrate 30 is loaded into a carrier head 20 by the transfer station 16. The carousel 18 then transfers the substrate through a series of one or more of the polishing stations 14, and finally returns the polished substrate to the transfer station 16. Each carrier head 20 receives and holds a substrate, and polishes it by pressing it against the polishing slab 100 on the platen 110. During polishing, the carrier heads rotate and laterally or radially oscillate.

Figure 2:
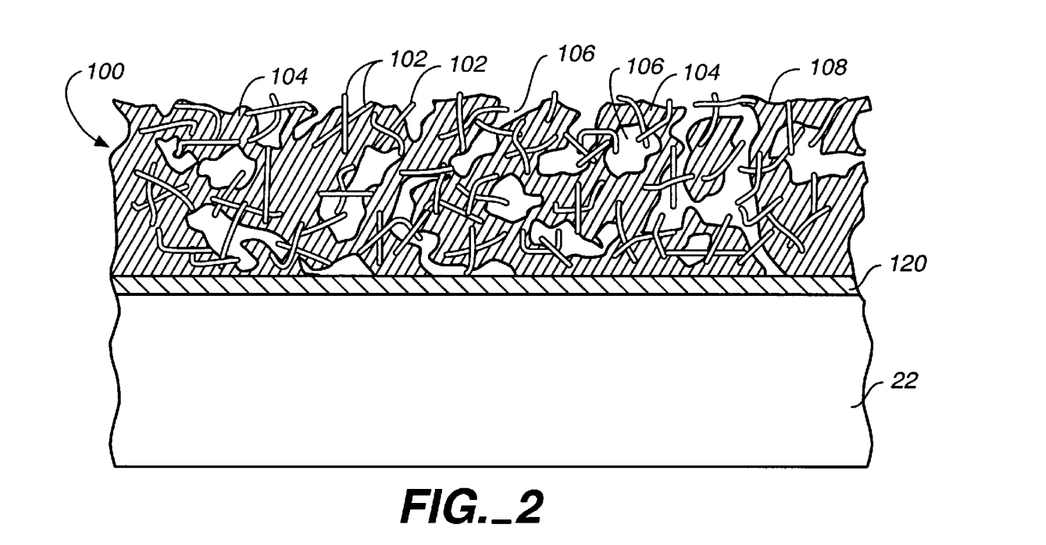
FIG. 2 is a schematic cross-sectional side view of the polishing pad of the present invention.

Referring to FIG. 2, the polishing pad 100 includes two primary components: a network or mesh of randomly oriented intertwined fibers 102, and a binder material 104 coalesced among the fibers 102 to hold them in the mesh. The polishing pad 100 has a rough surface 108 that is placed in contact with the substrate during polishing. The polishing material can be used in a circular polishing pad attached to a rotatable platen 22 with a water-resistant double-sided adhesive tape 120. The polishing material can thus form a single-layer pad, i.e., a compressible subpad may not be required.

The fibers 102 are composed of a material that is inert in the polishing process. The fibers can be generally brittle when leached with the binder material 104 and exposed to the shear forces in the polishing or conditioning environment. For example, the fibers can be formed of an organic material, such as cellulose, e.g., linen, cotton or wood, or a polymer material, such as a polyamide, e.g., Aramid™. Aramid fibers, which are available from DuPont Corporation, of Newark, N.J., have at least 85% of the amide linkages attached directly between two aromatic rings. The fibers can be arranged in the mesh with random orientations, and need not be oriented preferentially along a particular axis. The fibers can vary in length between about 50 and 1000 microns, e.g., between 100 and 500 microns, and the cross-sectional diameters of the fibers may vary between about 5 and 50 microns, e.g., between 10 and 30 microns.

The binder material 104 is also composed of a material that is inert in the polishing process and is generally brittle when exposed to the shear forces in the polishing or conditioning environment. For example, the binder material can be a porous polymer resin, such as a phenolic resin or epoxy resin. The binder material 104 is coalesced among the fibers 102 to bind the fibers into the mesh. However, the binder material 104 sticks mainly to the fibers and does not form a solid block, thereby leaving fairly large voids or pores 106 in the spaces between the fibers 102.

Since both the fibers 102 and binder 104 are fairly brittle, the resulting composite polishing pad has a fairly brittle surface texture when compared to conventional polishing pads. In short, the surface of the polishing pad is a rough, brittle mat of randomly oriented fibers. Since the pad is brittle, it has a relatively large tensile modulus and undergoes relatively little plastic deformation (in comparison to conventional non-fixed abrasive polishing pads such as the IC-1000 or Suba-IV). In addition, the composite polishing pad is friable, i.e., the surface has a tendency to crumble under frictional force, e.g., when exposed to the shear forces in the polishing or conditioning environment. It should be noted that the friability of the polishing pad may only occur on a microscopic level during polishing, i.e., it is not necessary that shedding from the pad be visually observed during polishing and conditioning. However, the friability of the polishing pad should be observable if the pad is scraped lightly with a razor blade.

Although the pad is brittle, the voids and binder material can provide the pad with a compressibility suitable for chemical mechanical polishing. Specifically, under an applied load, the voids can collapse to permit the pad to compress without breaking the linkages formed between the fibers by the binder material. This permits the polishing material to be elastically deformable during compression.

The specific polishing characteristics of the polishing pad 100 are determined by the composition and hardness of the fibers 102 and the binder material 104, the quantity of fibers 102, and the size and shape of the fibers 102, the size and shape of the pores in the pad, and the manufacturing process. In a polishing pad with phenolic resin and cellulose fibers, the ratio of fibrous material to binder material can be about 1:1 to 2:1, e.g., about 1.5:1 by weight. About half of the volume of the polishing pad can be take by the voids 106. In general, increased curing of the binder material material during manufacturing can cause the pad to become more brittle, whereas decreased curing can cause the pad to become less brittle. In general, using few fibers and packing the fibers less densely would increase the surface friction of the polishing pad and increase the polishing rate. Conversely, packing the fibers more densely would decrease the surface friction of the polishing pad, thus reducing the polishing rate.

If the surface friction of the polishing pad needs to be increased further, a small amount of an elastomer, such as a rubber, e.g., latex, can be added to the binder material. This can result in a polishing pad that is slightly "sticky" to provide a higher surface friction, while maintaining a pad that is sufficiently brittle under the lateral force from the substrate during polishing or conditioning. Other additives can include graphite to make the pad denser and more abrasive, and calcium celite (e.g., diatomaceous earth) to maintain the porosity of the fiber mesh. The additives can be soluble or insoluble in the binder material. Moreover, some additives can be integrated in the body of the fibers, rather than being dispersed in the binder material.

Since the pad material is brittle and friable, the fibers 102 and binder 104 "shed" easily. That is, under a lateral force, the fibers and binder material near the surface 108 of the polishing pad 100 break away from the body 110 of the polishing pad. However, since the pad is compressible, the fibers will remain in the matrix and are not torn away from the body of the polishing pad under a compressive force. For example, referring to FIG. 3, a substrate 10 passing over the surface of the polishing pad 100 during polishing will generate a downward force FD and a lateral force FL. The downward force FD will compress the region of the polishing pad directly below the substrate, although there may also be a rebound region. On the other hand, since the pad material is fairly brittle, the lateral force FL will tend to cause fragments 112 of the fibers 102 and the binder material 104 to break away from the body of the polishing pad, thus shearing away a very thin upper layer of the pad. This action might occur either from breakage of individual fibers, or from breakage of the binder material that results in an entire fiber coming free from the pad, or from breakage of chemical bonds between fibers. However, as previously noted, the fragmentation of the polishing pad surface may only occur on a microscopic level, i.e., it is not necessary that shedding from the pad be visually observed.

Figure 3:
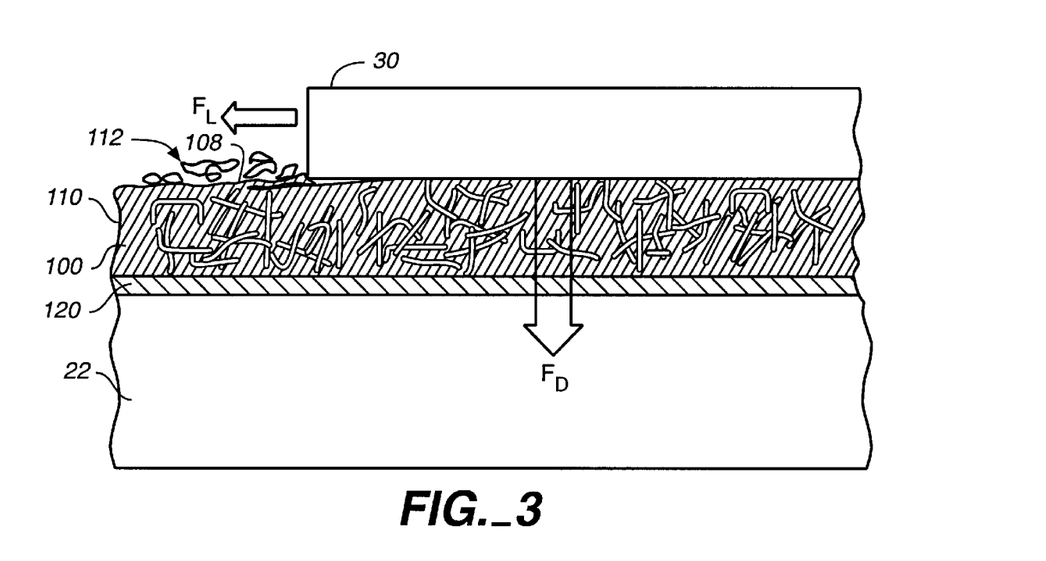
FIG. 3 is a schematic cross-sectional side view showing a substrate being polished with the polishing pad of FIG. 2.

Since the pad material is fairly homogenous and isotropic, with the fibers 102 dispersed through the pad at a uniform density and with random orientations, the polishing pad can maintain uniform mechanical properties as the top surface of the polishing pad is worn away. Therefore, the polishing pad should exhibit uniform surface friction throughout its lifetime. This can provide more uniform polishing rates, both during polishing of a single wafer and across wafer lots. In addition, since the polishing pad material sheds, the pad refreshes itself, thereby potentially eliminating the need for conditioning. Furthermore, a polishing pad composed of cellulose fibers and a phenolic resin binder material creates a polishing pad that can be thermally stable, i.e., its mechanical properties do not change sufficiently to affect polishing, over a wider range of temperatures than conventional pads.

Figure 4:
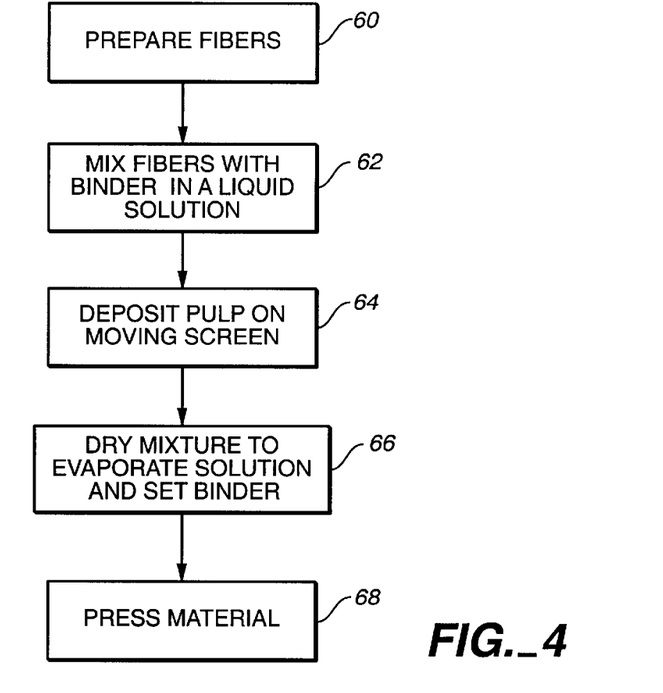
FIG. 4 is a flow chart of a method of manufacturing the polishing pad of FIG. 1.

The polishing pad 100 can formed using techniques generally known by manufacturers of automobile clutch and brake pads. In fact, a conventional automobile clutch or brake pad may be suitable for use in chemical mechanical polishing, thus providing a new use for a conventional structure. Referring to FIG. 4, the matrix of fibers is formed using a process similar to the Fourdrinier process. First, the fibers are prepared (step 60). Cellulose fibers can be created by mechanically pulping linen, cotton, wood or the like. Aramid fibers are available from DuPont Corporation, of Newark, N.J. The fibers are mixed with a liquid, such as a solution of the binder material, e.g., a phenol, and a liquid in which the binder material is soluble, e.g., an alcohol, to form a liquid pulp (step 62). The liquid pulp is then deposited on a screen or a continuous belt (step 64). As the liquid dries and drains off, the solution evaporates and the binder cures or sets to form the relatively brittle resinous binder material, e.g., the phenolic resin (step 66). The material may then be pressed to remove more liquid and create weak chemical bonding between the fibers (step 68).

Figure 5:
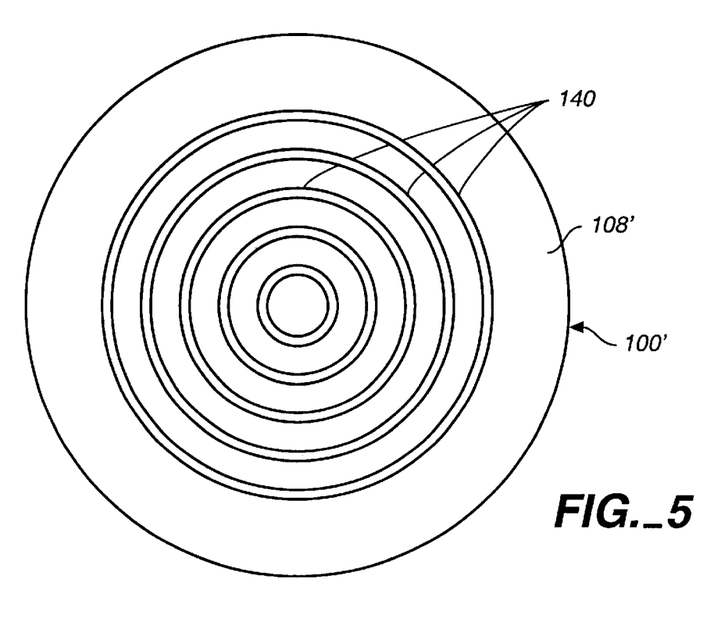
FIG. 5 is a schematic top view of a polishing pad with grooves.

As shown in FIG. 5, the surface of the polishing pad 100' can be textured prior to and/or during engagement with the substrate surface. Specifically, grooves or perforations 140 can be formed in the top surface 108' of the polishing pad. In one implementation, the grooves 140 are concentric circles with a depth of about 0.02 inches, a width of about 0.10 inches and a pitch of about 0.25 inches. However, grooves and perforations may not be necessary, as slurry can be trapped in the pores 108 in the fiber mesh and transported by the polishing pad.

Figure 6:
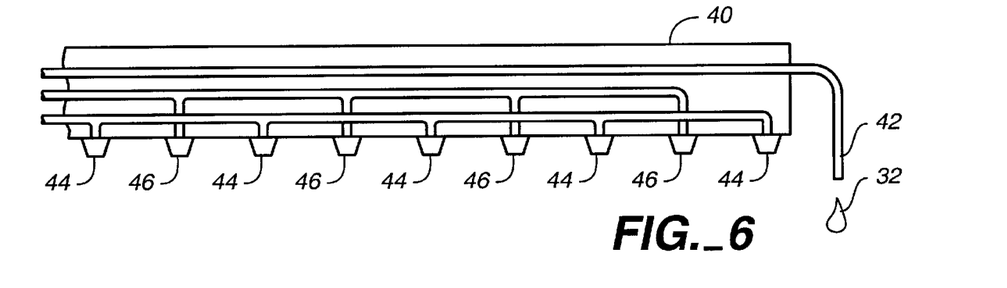
FIG. 6 is a schematic side view of a slurry/rinse arm polishing extending over a polishing pad.

As shown in FIG. 6, each polishing station of CMP apparatus 10 can include a combined slurry/rinse arm 40 that projects over the surface of the polishing pad 100. The slurry/rinse arm 40 can include one or more slurry supply tubes 42 connected to a slurry delivery system to provide a slurry 32 to the surface of the polishing pad. Typically, sufficient slurry is provided to wet the entire polishing pad. The slurry/rinse arm 40 also includes several spray nozzles 44 to create high-pressure jets of a cleaning fluid, e.g., deionized water. The jets of cleaning fluid provide a high-pressure rinse of the polishing pad at the end of each polishing cycle in order to remove used slurry and polishing debris from the polishing pad. The slurry/rinse arm 40 can also include several air nozzles 46 that direct high-pressure jets of air into the polishing pad. These high-pressure jets purge the cleaning fluid from of the polishing pad and prevent dilution of the slurry during the next polishing cycle. Alternatively, the spray nozzles 44 can be connected to both a cleaning fluid source and a pressurized air source in order to perform both the spray rinse and the air purge of the polishing pad, or to a vacuum source to suction cleaning fluid from the polishing pad.

Figure 7A:
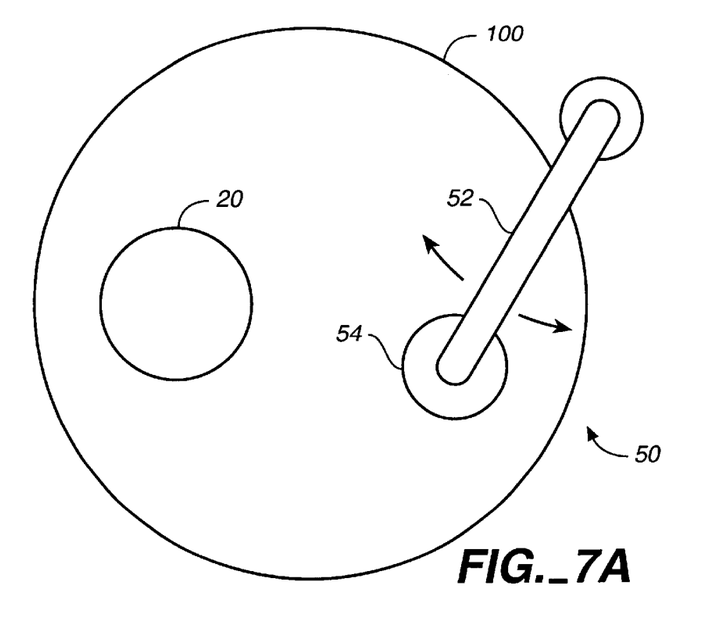
FIG. 7A is a schematic top view of a polishing apparatus including a conditioning device.
Figure 7B:
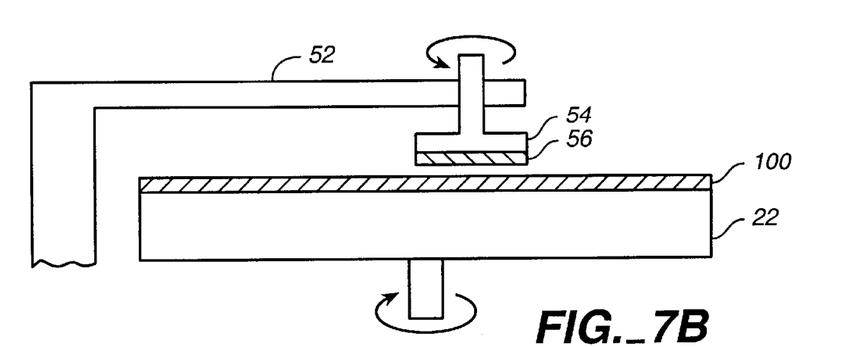
FIG. 7B is a side view of the conditioning device of FIG. 7A.

As shown in FIGS. 7A and 7B, each station of the CMP apparatus 10 can include a conditioning apparatus 50. Each pad conditioner apparatus 50 has an oscillating arm 52 that holds an independently rotating conditioner head 54. A similar conditioner apparatus is described in U.S. application Ser. No. 09/052,798, filed Mar. 31, 1998, assigned to the assignee of the present application, the entirety of which is incorporated herein by reference. If required, the conditioner apparatus maintains the condition of the polishing pad so that it will provide uniform polishing. Conditioning may also be needed for an initial break-in of the polishing pad. A circular sheet of polishing pad material 56 may be secured to the underside of the conditioner head. In operation, the conditioner head 54 rotates as the arm 52 oscillates to sweep the conditioner head across the polishing pad 100 with the conditioning material 56 pressed against the polishing pad 100. Thus, rather than an expensive diamond disk, the same material that performs the polishing can be used to condition the polishing pad. In general, conditioning of the brittle polishing pad could be performed by other devices in the polishing apparatus. For example, if a carrier head includes a retaining ring with grooves formed on the underside for slurry transport, the sharp edges of the grooves may act to condition the polishing pad and improve the polishing rate.

In one experiment, a "light brown" fibrous material, composed of paper or Aramid fibers in a resin was obtained from Raybestos Corp., of Crayfordsville, Ind. The material was cut into a 20-inch diameter pad with thickness of about 0.04 inches, and affixed to a platen of a MIRRA® polishing machine with double-sided adhesive. No grooves were formed in the pad. The pad was rinsed with high-pressure water prior to polishing, and showed good wetability. One patterned wafer was polished with Rodel SS-12 slurry on a Titan Head™ wafer carrier using at a substrate pressure of 2 psi. The platen rotation rate was 93 rpm, and the carrier head rotation rate was 87 rpm. No conditioning was performed. The polishing pad successfully polished the substrate with a planarity (within-wafer nonuniformity) superior to that of a conventional IC-1000/Suba-IV pad stack.

In another experiment, a series of substrates were polished under the conditions described above. The substrates included both "blank" wafers with a layer of thermal oxide, and patterned wafers. Before polishing of a patterned wafer, the polishing rate was about 200–300 Å/min, whereas after polishing of a patterned wafer, the polishing rate rose to about 600–650 Å/min and remained relatively constant through 140 minutes of polishing. Without being limited to any particular theory, the patterned wafer may have abraded the top surface of the polishing pad so as to improve the polishing rate. The surface temperature of the polishing pad remained constant at about 85° F. By implementing the air purge of water from the pad, a grooved retaining ring, and like-material pad conditioning, as described above, the polishing rate was increased to about 1200 Å/min.

Figure 8A:
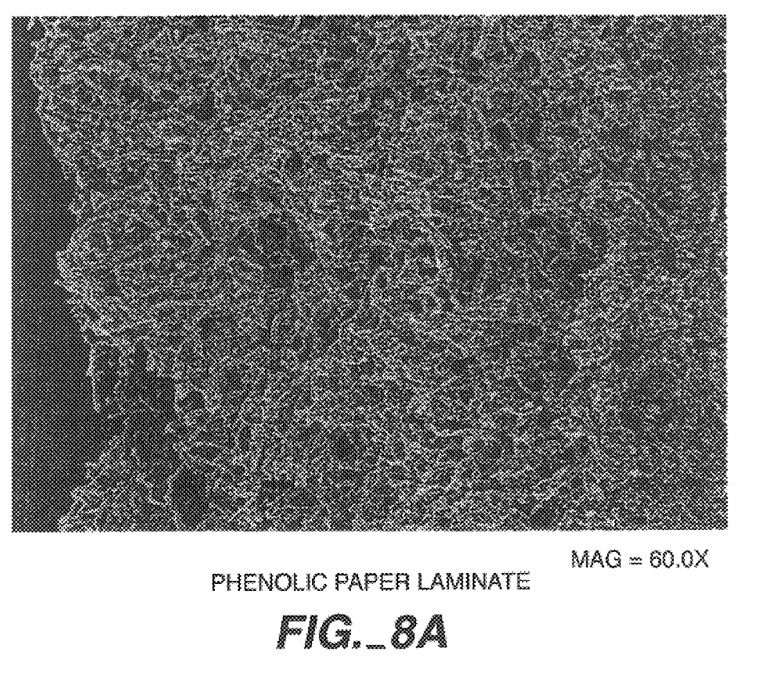
FIGS. 8A, and 8B are photographs of the surface texture of the polishing pad at magnifications of ×40 and ×200, respectively.
Figure 8B:
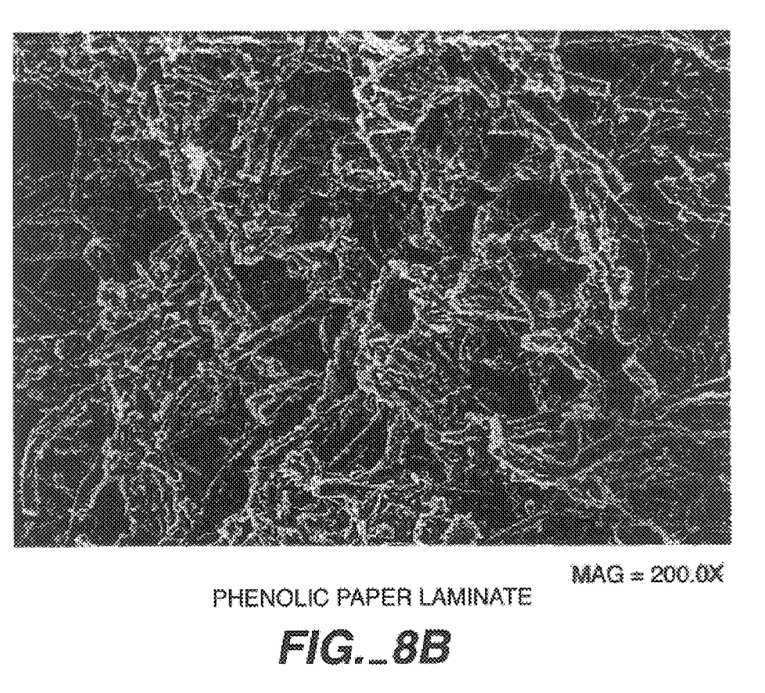

Photographs of the polishing pad material used in the above experiments at magnifications of ×40 and ×200 are shown in FIGS. 8A, and 8B, respectively. A comparison of the physical characteristics of a sample of the polishing pad material used in the above experiments versus several conventional polishing pads is given in the table below:

|  | New pad material | IC-1000 | Suba-IV |
| --- | --- | --- | --- |
| Aprox. average tensile strength (psi) | 1350 | n/a | 2800 (transverse to fiber orientation) |
| Aprox. average yield point (psi) | 1350 | n/a | 900 (transverse to fiber orientation) |
| Elasticity | up to 1% elongation before breaking | n/a | up to 25–30% elongation before breaking |
| Average tensile modulus (psi) | 3–5 × $10^5$ | n/a | 3–4 × $10^4$ |
| Aprox. average flexural modulus | 2 × $10^5$ | n/a | 1 × $10^4$ |
| Compressibility modulus (psi) | 8 × $10^4$ | n/a | 4 × $10^4$ |
| Hardness (Shore D) | 59–65 | 60 | n/a |
| Abrasion Resistance | poor | good | good |
| Water Absorption | good (40% by weight) | poor (<1% by weight) | good |

In general, a material may be considered brittle if it undergoes little elongation (in comparison to conventional polishing pad materials), e.g., less than 5% elastic or plastic deformation, prior to breaking. For example, the polishing pad can have an elongation less than about 3%, less than about 2%, or less than about 1%, prior to breaking. The polishing pad 100 can have a tensile modulus greater than $10^5$ psi, e.g., greater than 2×$10^5$ psi, or greater than 3×$10^5$ psi, and a flexural modulus greater than 5×$10^4$ psi, e.g., greater than $10^5$ psi. Another indication that a material is brittle is if the tensile point, i.e., the force or pressure at which the material breaks, does not differ significantly, e.g., less than 5% different for polishing pad materials, from the yield point, i.e., the force or pressure at which the material begins to deform.

Thus, the polishing pad should have a yield point that is substantially the same as the tensile point. The difference between the yield and tensile point can be less than 5%, e.g., less than 1%. Tests of the elongation, yield point, tensile point and tensile modulus may be performed with the ASTM D638 test, and tests of the flexural modulus may be performed with the ASTM D790 test.

The brittle polishing pad 100 can be used to polish metals such as copper, dielectrics (including oxides and nitrides) such as silicon oxide, and semiconductors such as silicon. The multiplaten architecture of CMP apparatus 10 permits a wide variety of polishing processes to be performed using the brittle polishing pad 100. In a typical implementation, substrate may be polished with brittle polishing pads at the first two polishing stations, and then buffed with a conventional soft polishing pad at the final polishing station. Alternatively, the brittle polishing pad at the first platen may be followed by a conventional standard polishing pad or a fixed abrasive polishing pad at the second platen, or a conventional standard polishing pad or a fixed abrasive polishing pad at the first platen may be followed by a brittle polishing pad at the second platen.

Several embodiments of the present invention have been described. Nevertheless, it will be understood that various modifications may be made without departing from the spirit and scope of the invention. Accordingly, other embodiments are within the scope of the following claims.

What is claimed is:

1. A chemical mechanical polishing apparatus, comprising:
   a carrier head to hold a substrate;
   a polishing pad including polishing layer with a mesh of fibers and a brittle binder material holding the fibers in the mesh, the binder material coalesced among the fibers to leave pores in the interstices between the fibers of the mesh, wherein the fibers and binder material provide the polishing layer with a brittle structure; and
   a supply port to dispense a polishing liquid to the polishing pad.

2. The apparatus of claim 1, further comprising a rotatable platen, wherein the polishing pad is secured to a surface of the platen.

3. The apparatus of claim 1, wherein the polishing layer has a tensile modulus greater than about $10^5$ psi.

4. The apparatus of claim 2, wherein the tensile modulus is greater than about $3 \times 10^5$ psi.

5. The apparatus of claim 1, wherein the polishing layer elongates less than about 5% before breaking.

6. The apparatus of claim 5, wherein the polishing layer elongates less than about 2% before breaking.

7. The apparatus of claim 6, wherein the polishing layer elongates less than about 1% before breaking.

8. The apparatus of claim 1, wherein the polishing layer undergoes elastic deformation during compression.

9. The apparatus of claim 1, wherein the fibers include cellulose.

10. The apparatus of claim 9, wherein the fibers are formed from linen or wood.

11. The apparatus of claim 1, wherein the fibers include cotton.

12. The apparatus of claim 1, wherein the fibers include a polyamide.

13. The apparatus of claim 12, wherein the fibers are formed from Aramid.

14. The apparatus of claim 1, wherein the binder includes a resin.

15. The apparatus of claim 13, wherein the resin includes a phenolic resin.

16. The apparatus of claim 1, wherein the ratio of fibers to binder in the polishing layer is about 1:1 to 2:1 by weight.

17. The apparatus of claim 1, wherein the pores occupy about half of the volume of the polishing layer.

18. The apparatus of claim 1, wherein the fibers are oriented substantially randomly throughout the polishing layer.

19. The apparatus of claim 1, wherein the polishing layer includes one or more of the following:

graphite, calcium celite, and an elastomer.

20. The apparatus of claim 1, wherein the polishing layer has an average yield point and an average tensile strength that differ by less than 5%.

21. The apparatus of claim 20, wherein the polishing layer has an average yield point and an average tensile strength that differ by less than 1%.

22. The apparatus of claim 1, further comprising a plurality of nozzles to spray a cleaning solution onto the polishing pad and remove slurry from the polishing pad.

23. The apparatus of claim 1, further comprising a plurality of nozzles to direct jets of air onto the polishing pad and remove the cleaning solution from the polishing pad.

24. A chemical mechanical polishing apparatus, comprising:

a carrier head to hold a substrate;

a polishing pad including a layer of polishing material having a mesh of cellulose fibers and a phenolic resin binding the fibers in the mesh, the resin coalesced around the fibers to leave pores in the interstices in the fiber mesh; and a supply port to dispense a polishing liquid to the polishing pad.

25. A chemical mechanical polishing apparatus, comprising:

a carrier head to hold a substrate;

a polishing pad including a layer of polishing material having a mesh of cotton fibers and a phenolic resin binding the fibers in the mesh, the resin coalesced around the fibers to leave pores in the interstices in the fiber mesh; and a supply port to dispense a polishing liquid to the polishing pad.

26. A chemical mechanical polishing apparatus, comprising:

a carrier head to hold a substrate;

a polishing pad including a layer of polishing material includes a mesh of fibers and a binder holding the fibers in the mesh, the binder coalesced among the fibers to leave pores in the interstices between the fibers of the mesh, wherein the fibers and binder provide the material with an average yield point and an average tensile strength that substantially equal; and a supply port to dispense a polishing slurry to the polishing pad.

* * * * *